United States Patent
Lang et al.

[11] Patent Number: 6,115,633
[45] Date of Patent: Sep. 5, 2000

[54] IMPLANTABLE STIMULATOR

[75] Inventors: Volker Lang, Herzogenaurach; Armin Bolz, Erlangen, both of Germany

[73] Assignee: BIOTRONIK Mess-und Therapiegeraete GmbH & Co. Ingenieurbuero Berlin, Berlin, Germany

[21] Appl. No.: 08/958,199

[22] Filed: Oct. 27, 1997

[30] Foreign Application Priority Data

Oct. 28, 1996 [DE] Germany ............................ 196 45 291
Dec. 18, 1996 [DE] Germany ............................ 196 54 494

[51] Int. Cl.[7] .................................................... A61N 1/365
[52] U.S. Cl. ............................................ 607/17; 600/547
[58] Field of Search .................................. 607/9, 17, 24; 600/547

[56] References Cited

U.S. PATENT DOCUMENTS

| | | |
|---|---|---|
| 4,686,987 | 8/1987 | Salo et al. ..................................... 607/9 |
| 4,865,036 | 9/1989 | Chirife . |
| 5,174,299 | 12/1992 | Nelson . |
| 5,183,040 | 2/1993 | Nappholz et al. . |
| 5,213,098 | 5/1993 | Bennett et al. . |
| 5,330,505 | 7/1994 | Cohen . |

FOREIGN PATENT DOCUMENTS

| | | |
|---|---|---|
| 0191404 | 8/1986 | European Pat. Off. . |
| 0465241 | 1/1992 | European Pat. Off. . |
| 0474958 | 3/1992 | European Pat. Off. . |
| 0634192 | 1/1995 | European Pat. Off. . |
| 3903323 | 12/1989 | Germany . |

OTHER PUBLICATIONS

P.Profos et al., Published, Handubch der industriellen Messtechnik [Handbuch of Industrial Measuring Technology 5th Edition, R. Oldenbourg Verlag, Munich 1992, pp. 732–734.

*Primary Examiner*—Jeffrey R. Jastrzab
*Attorney, Agent, or Firm*—Venable; Robert Kinberg; Michael P. Leary

[57] ABSTRACT

An implantable stimulator for treating arrhythmic function disturbances of a heart, comprising; a stimulation electrode for transmitting stimulation pulses to the heart, a pulse generator that is connected to the stimulation electrode for generating the stimulation pulses, a control unit connected to the pulse generator for controlling the pulse emissions, a hemodynamic sensor for controlling the pulse emission as a function of the cardiac pumping performance, the hemodynamic sensor including; two measuring electrodes located in or in electrical contact with a blood vessel, for measuring the blood impedance dependent on the blood throughput, a signal generator that generates an AC voltage for generating a test signal for impedance measurement, an electrical measuring device connected to the twvo measuring electrodes for determining the blood throughput as a function of the measured electrical signal; and a blood throughput signal-analysis unit for recognizing an arrhythmic cardiac finction disturbance using the measured throughput quantity.

11 Claims, 4 Drawing Sheets

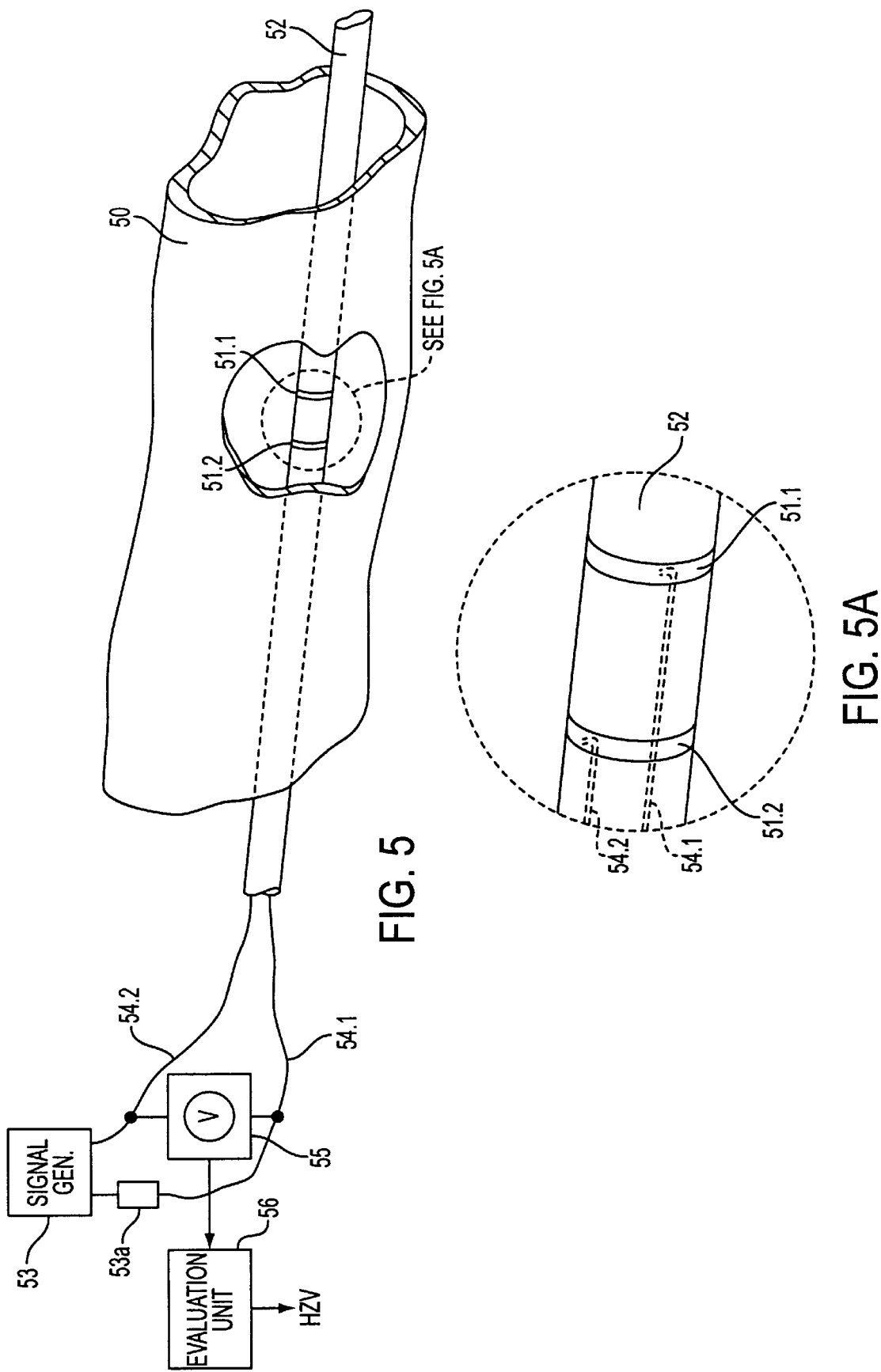

IMPLANTABLE STIMULATOR

BACKGROUND OF THE INVENTION

The invention relates to an implantable stimulator for treating arrhythmic function disturbances of a heart, comprising: a stimulation electrode for transmitting stimulation pulses to the heart, the electrode being adapted to be disposed in one of the heart and the vicinity thereof, a pulse generator that is connected on an output side to the stimulation electrode for generating the stimulation pulses, a control unit that is connected on an output side to the pulse generator for controlling the pulse emission by the pulse generator, and a blood throughput device for controlling the pulse emission as a function of the cardiac pumping performance.

It is known to treat arrhythmic cardiac function disturbances, such as ventricular fibrillation, with the use of implantable cardioversion devices—also called defibrillators—that detect spontaneous cardiac signals, typically using an electrode disposed endocardially in the ventricle, and, when ventricular fibrillation or flutter is detected, transmit a high-energy current pulse—referred to hereinafter as defibrillation pulse—to the heart; the intensity of the pulse leads to a stimulation and depolarization of virtually all regions of the heart, so the arrhythmic state is ended and the normal sinus rhythm can reassume control of the heartbeat.

This type of identification of an arrhythmic cardiac state employing the evaluation of the intracardially-detected spontaneous cardiac signals is, however, susceptible to a wide range of possible interferences. For example, the amplitude of the spontaneous cardiac signals can be subjected to temporal fluctuations, e.g. in day/night rhythm, which impede reliable detection of arrhythmic cardiac states. It is also possible that electromagnetic interference signals are erroneously identified as intracardial EKG signals. Furthermore, the danger exists that spontaneous atrial cardiac signals electrically overspeak on the ventricle, so a relatively harmless atrial fibrillation is erroneously identified as ventricular fibrillation, and a defibrillation pulse is triggered, although the patient is not in a critical state. Thus, the reliability of the detection of arrhythmic cardiac states is unsatisfactory in the known defibrillators.

Cardiac pacemakers are also known for treating a disturbed stimulus transmission from the atrium to the ventricle. Pacemakers of this type usually detect spontaneous atrial actions using an electrode that is disposed endocardially in the atrium, and, following each spontaneous atrial action, respectively transmit a stimulation pulse to the ventricle with a delay of a predetermined AV transmission time. The delay of the ventricular stimulation after each atrial action is necessary to permit an optimum chamber filling prior to the contraction as a prerequisite for good cardiac pumping performance; the optimum value of the AV transmission time is individual to the respective pacemaker patient, and can also be susceptible to temporal fluctuations. Hence, a problem associated with the known pacemakers of this type is that the AV transmission time is not set optimally in most cases, leading to a reduction in the cardiac pumping performance.

It is therefore the object of the invention to provide an implantable stimulator in which the control of the pulse emission for ending arrhythmic disturbances in function is better adapted to the needs of the patient.

SUMMARY OF THE INVENTION

This object is accomplished in the context of an implantable stimulation device, as first defined above, wherein the blood throughput device comprises a hemodynamic sensor including; two measuring electrodes spaced apart and located outside of the heart and one of in a blood vessel and in electrical contact with a blood vessel, for measuring the blood impedance dependent on the blood throughput, a signal generator that generates an AC voltage in a range below 10 kHz for generating a test signal for impedance measurement, the generator being connected on the output side to one of (1) the to measuring electrodes by way of a series resistor for reducing the measured current, and (2) to two field electrodes for generating an electrical field between the two measuring electrodes, an electrical measuring device connected to the two measuring electrodes for determining the blood throughput as a function of the measured electrical signal; and a blood throughput signal-analysis unit connected on the input side to the electrical measuring device and connected on the output side to the control unit for recognizing an arrhythmic cardiac fimction disturbance using the measured throughput quantity.

The invention includes the technical teaching of controlling the pulse emission in a generic implantable stimulator as a function of the cardiac pumping performance, with the cardiac pumping performance being detected by a hemodynamic sensor that detects the blood throughput in or at a blood vessel. It has proven particularly advantageous to dispose the hemodynamic sensor in the vena cava or pulmonary artery.

The term stimulator as used hereinafter particularly encompasses cardioverters and defibrillators, but also modern, multi-functional pacemakers; the principle of the invention can also be applied in therapy for certain tachycardiac states and ventricular flutter and, possibly, cardiac arrest.

The hemodynamic sensor can quantify the flow speed of the blood, for example, or, in special applications, only supply yes/no information regarding the blood throughput.

In an advantageous embodiment, the hemodynamic sensor includes a heatable resistor element that has a temperature-dependent electrical resistance and is disposed to be thermally contacting for a blood vessel for heat dissipation as a function of the quantity of flowing blood. The resistor element can be heated electrically, for example, in that it is connected to a voltage source so the element heats up due to ohmic losses in its interior. It is also possible, however, to heat the resistor element indirectly, for which purpose a separate electrical heating element is suitable. The temperature of the resistor element increases as a consequence of the heat dissipation until an equilibrium is established between the supplied energy, on the one hand, and the energy carried off due to heat conduction and convection from the blood flowing past, on the other hand. Because the energy carried off due to convection increases with the flow speed of the blood flowing past, a measurement of the equilibrium temperature permits the determination of the flow speed. Thus, with a low flow speed, only a small quantity of heat is dissipated through convection, so a relatively high temperature gradient must build up at the resistor element to allow the supplied heat to be dissipated through heat conduction, which results in a relatively high temperature of the resistor element. With an increasing flow speed of the blood flowing past, a correspondingly larger quantity of heat is dissipated through convection, so the temperature gradient at the resistor element can decrease, leading to a reduction in the temperature of the resistor element.

If the temperature dependency of the electrical resistor element is known, the temperature of the resistor element can be easily calculated from the electrical resistance of the resistor element. In accordance with Ohm's law, the electrical resistance of the resistor element results from the applied heating voltage and the heating current flowing through the resistor element. The electrical resistance of the resistor element therefore reflects the flow speed of the blood in the respective blood vessel, and thus permits an assessment of the cardiac pumping performance. It is particularly advantageous to integrate the resistor element with an amplifier on a chip, resulting in a small structural size of the sensor.

In contrast, in a preferred variation of the invention, the hemodynamic sensor detects the impedance of the blood, based on the surprising realization that the blood impedance is a function of, among other factors, the flow speed. In this variation of the invention, therefore, the hemodynamic sensor has two measuring electrodes, which are disposed in the blood vessel and thus permit a measurement of the blood impedance. In the preferred embodiment of this variation, the two measuring electrodes are connected to a signal generator that is integrated into the stimulator and generates an electric test signal, which is transmitted to the two measuring electrodes for impedance measurement. A current-measuring device that is likewise integrated into the stimulator measures the current flux via the two measuring electrodes, permitting a subsequent calculation of the blood impedance, which reflects the flow speed of the blood and thus the cardiac pumping performance.

In the preferred embodiment of this variation, the two measuring electrodes are integrated into the catheter that is inserted into the heart for positioning the stimulation electrode. With the integration of the hemodynamic sensor into the catheter, the stimulator of the invention can advantageously be implanted without additional efforts, because the catheter is necessary anyway for positioning the stimulation electrode. The two measuring electrodes are preferably disposed in the catheter wall, with axial spacing from one another, at a position that is outside of the heart once implantation is complete.

In the blood vessel, the two measuring electrodes can be disposed one behind the other in the flow direction, or adjacently to one another transversely to the flow direction, to take into consideration the anisotropy of the blood impedance, which is based on the fact that the erythrocytes in a blood flow are oriented among themselves in a predominant direction.

In the preferred variation of the invention, to detect spontaneous cardiac signals and control the pulse emission as a function of the measured blood flow, on the one hand, and the spontaneous cardiac signals, on the other hand, the control unit serving to control the pulse emission is connected on the input side to the stimulation electrode or a further, preferably endocardial, electrode. The pulse emission control is effected not only as a function of the measured blood flow, but also as a function of the spontaneous cardiac signals, and can thus be adapted better to the patient's needs, because the physical state of the patient can be assessed better by the control unit based on the greater variety of diagnostic information. In addition, interference signals that only affect a single input value can be suppressed by this procedure. For example, it is conceivable that the measured spontaneous cardiac signals are distorted by electromagnetic interference signals, while the measured pumping performance is extensively undistorted. The evaluation of different signals presents the option of a mutual plausibility check between the different signals for suppressing interferences.

To evaluate the spontaneous cardiac signals, in one variation of the invention, the control unit includes a signal-analysis unit that is connected on the input side to the electrode serving to detect the spontaneous cardiac signals, and, using the measured spontaneous cardiac signals, determines whether a cardiac function disturbance is present. This is particularly advantageous in an embodiment of the invention in a defibrillator, in which the signal-analysis unit permits a detection of tachycardia or arrhythmic cardiac function interferences, such as ventricular fibrillation, and when such a cardiac function interference is detected, the unit generates a corresponding control signal. The emission of defibrillation pulses is effected not only as a function of the spontaneous cardiac signals, but is also influenced by the cardiac pumping performance measured by the hemodynamic sensor. As already mentioned, this permits the elimination of interference signals that only affect one of the two input signals. This means that a defibrillation pulse is only emitted if the spontaneous cardiac signals indicate a ventricular fibrillation and the cardiac pumping performance has fallen below a predetermined limit value, which is essentially the case in ventricular fibrillation. As in the embodiment of the invention in other stimulators, a logic unit that also permits the incorporation of further diagnostic values such as the physical activity detected by an activity sensor, or the respiratory minute value that can be determined through measurement of the intracardial impedance, is suitable for correlating the input signals in this manner.

In an advantageous variation of the invention, it is further provided that the hemodynamic sensor is not operated continuously as a means of decreasing the energy consumption during stimulator operation, which is particularly advantageous if the hemodynamic sensor has, as described above, a heatable resistor element, because in this case the operation of the hemodynamic sensor is associated with a relatively high energy consumption. In this variation of the invention, the activation of the hemodynamic sensor is effected by a controllable switching element, with the switching element being actuated, for example, through timing or remote control via a telemetry receiver. In one embodiment of the concept of the invention in a defibrillator, it is particularly advantageous to activate the hemodynamic sensor when the evaluation of the spontaneous cardiac signals indicates an arrhythmic cardiac state. The measurement result of the hemodynamic sensor then permits a plausibility check, and thus prevents the emission of a contra-indicated defibrillation pulse.

BRIEF DESCRIPTION OF THE DRAWINGS

Other advantageous modifications of the invention are characterized in the dependent claims and described in detail in the following description of the preferred embodiment in conjunction with the figures. Shown are in:

DETAILED DESCRIPTION OF THE INVENTION

Figure 1:
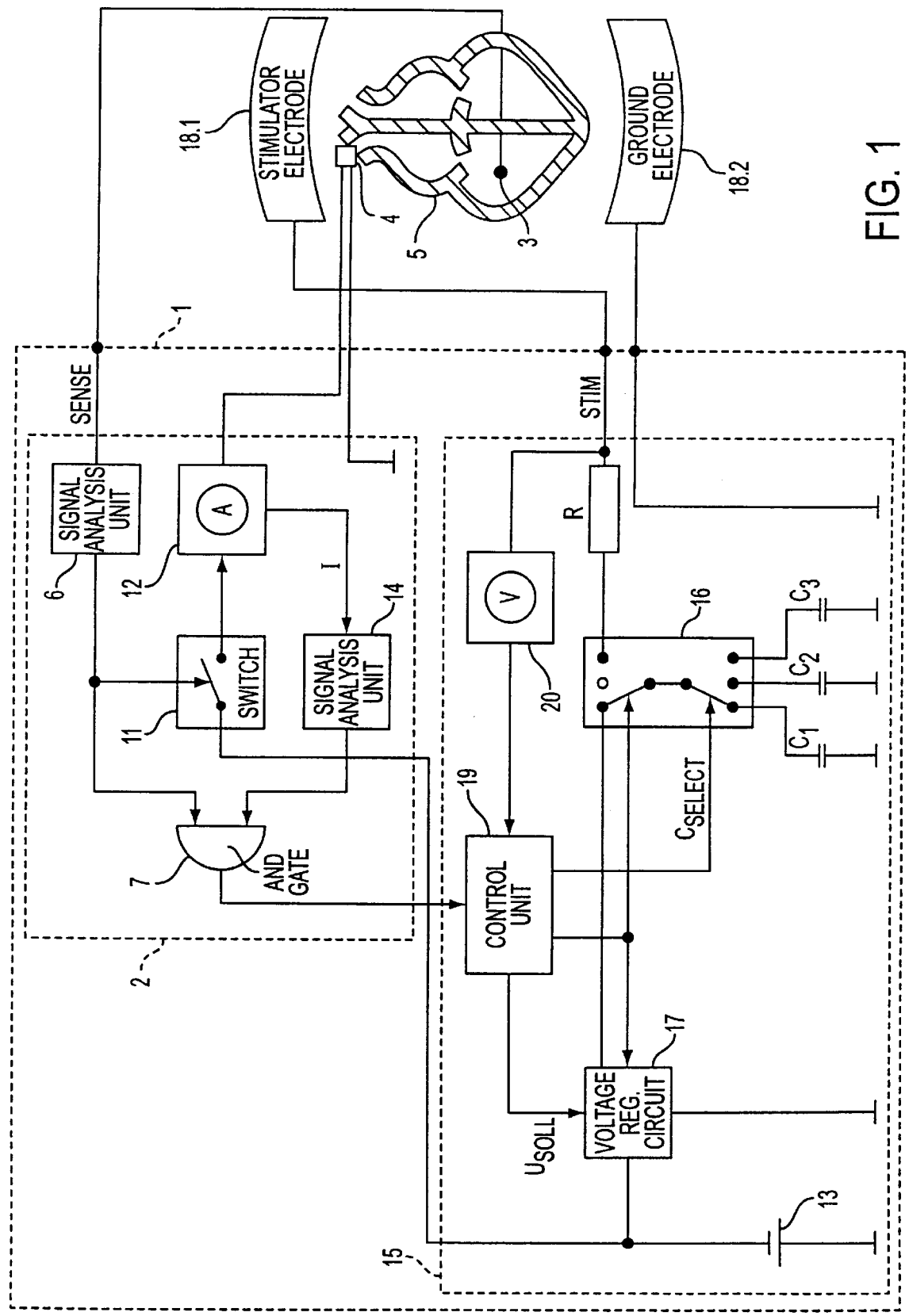
FIG. 1 is a preferred embodiment of the invention, an implantable defibrillator in which a defibrillation pulse is only emitted upon a reduction in the cardiac pumping performance, with the cardiac pumping performance being measured by a hemodynamic sensor.

The implantable defibrillator 1, shown in a block diagram in FIG. 1, permits an automatic recognition and termination of an arrhythmic cardiac state through the emission of a high-energy defibrillation pulse which, due to its intensity, leads to a stimulation and depolarization of virtually all regions of the heart, so the arrhythmic state is ended and the normal sinus rhythm can again assume control of the heartbeat.

Figure 3A:
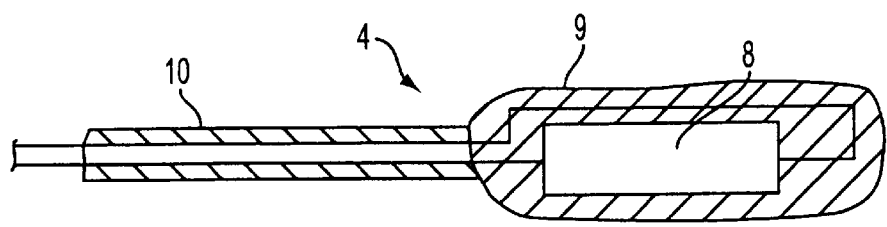
FIG. 3a is a preferred embodiment of a hemodynamic sensor for the above-described embodiments.

The pulse emission is controlled by a control unit 2, which is connected on the input side to an electrode 3 disposed endocardially in the ventricle for assessing the cardiac function, on the one hand, and on the other hand to a hemodynamic sensor 4 disposed in the vena cava, the function of which sensor is illustrated in detail in FIG. 3a.

The electrode 3 permits the detection of spontaneous cardiac signals and the recognition of an arrhythmic cardiac state, while the hemodynamic sensor 4 detects the flow speed of the blood and therefore permits an assessment of the pumping performance of the heart 5. The control of the pulse emission using different input signals offers various advantages. On the one hand, the control unit 2 obtains a more precise picture of the cardiac function based on the different diagnostic input signals, so the control of the pulse emission can be better adapted to the patient's needs. On the other hand, based on the different input signals, it is possible to suppress the interference signals that affect only one of the input signals. This type of mutual plausibility checking of the two input signals increases reliability in recognizing arrhythmic cardiac function interferences, and extensively avoids erroneous detections and contra-indicated defibrillation pulses.

For recognizing an arrhythmic cardiac state, the control unit 2 has a signal-analysis unit 6, which is connected on the input side to the endocardial electrode 3 for receiving the spontaneous cardiac signals. When an arrhythmic cardiac state is detected, the signal-analysis unit 6 generates a corresponding control signal with a logical HIGH level that is supplied to the AND gate 7 for further evaluation.

Moreover, the recognition of an arrhythmic cardiac state by the signal-analysis unit 6 also leads to the activation of the hemodynamic sensor 4, which then determines the pumping performance of the heart 5. To conserve energy, the hemodynamic sensor 4 is switched off during normal operation of the defibrillator 1, and is only switched on by the signal-analysis unit 6 if an arrhythmic cardiac state is recognized, so the plausibility check can be performed using the measured cardiac pumping performance, and a contraindicated emission of a defibrillation pulse can be prevented.

As can be seen from FIG. 3a, the hemodynamic sensor 4 essentially comprises a resistor element 8, and is disposed in the vena cava. To prevent electrical contact with the blood flowing past, or with the wall of the blood vessel, the resistor element 8 is encapsulated by an electrically-insulating but thermally well-conducting mass 9, through which the supply lines 10 are guided.

Figure 4:
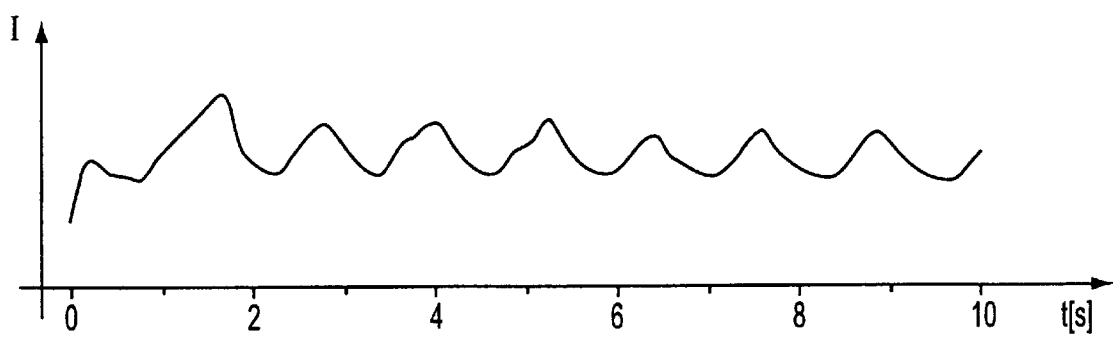
FIG. 4 is the course over time of the current flux through the hemodynamic sensor shown in FIG. 3a, and FIG. 5 is a further embodiment of a hemodynamic sensor in which the impedance of the blood is measured for determining the cardiac pumping performance.

For activating the hemodynamic sensor 4, the sensor is connected via the controllable switching element 11 and the current-measuring device 12 to the battery 13 of the defibrillator 1, so an electrical current flows through the resistor element 8. Because of the ohmic losses inside the resistor element 8, its temperature increases until an equilibrium is achieved between the supplied electrical energy, on the one hand, and the thermal energy carried off through heat conduction and convection by the blood flowing past, on the other hand. Because the energy carried off through convection increases with the flow speed of the blood flowing past, a measurement of the equilibrium temperature permits a determination of the flow speed. Hence, at a low flow speed, only a small quantity of heat is carried off through convection, so a relatively high temperature gradient must first build up at the resistor element 8 to enable dissipation of the supplied heat through heat conduction, which results in a relatively high temperature of the resistor element 8. With increasing flow speed of the blood flowing past, correspondingly more heat is carried off through convection, so the temperature gradient at the resistor element 8 can decrease, resulting in a temperature drop of the resistor element 8. The flow speed of blood in the vena cava, and thus the cardiac pumping performance, can be determined through a measurement of the electrical current through the resistor element 8, because the ohmic resistance of the resistor element 8 is temperature-dependent. FIG. 4 shows, by way of example, the pulsing course of the electrical current through the resistor element 8 for a normal heart rate. The fluctuations of the current flux that reflect the cardiac rhythm can be seen clearly here. The output signal of the current-measuring device 12 is therefore supplied to a signal-analysis unit 14, which uses it to calculate the pumping performance of the heart 5, and compares this value to a predetermined limit value. If the pumping performance drops below the predetermined limit value, the signal-analysis unit 14 assumes the cause to be an arrhythmic cardiac state, and, on the output side, consequently generates a corresponding signal having a HIGH level that is subsequently supplied to the AND gate 7 for further processing.

The AND gate 7 serves to trigger the pulse generator 15 for emitting a defibrillation pulse in the event of an arrhythmic cardiac state, in which case, because of the AND link, a defibrillation pulse is only emitted if both the evaluation of the spontaneous cardiac signals and the evaluation of the pumping performance of the heart 5 indicate a ventricular fibrillation or flutter. This plausibility check prevents a contra-indicated emission of a defibrillation pulse when a disturbed signal detection from the heart 5 is present. In particular, this prevents both an erroneous detection of ventricular flutter when electrical overspeak of a relatively harmless atrial fibrillation occurs from the atrium on the ventricle, and the emission of a defibrillation pulse that would be contra-indicated in this case.

The defibrillation pulses are generated by the pulse generator 15, which is actuated by the AND gate 7 of the control unit 2 and, in the event of an arrhythmic cardiac state, first connects one of the buffer capacitors $C_1$, $C_2$, $C_3$ to the voltage-regulating circuit 17 through the switching means 16 during a charging phase, charging the buffer capacitor. The voltage-regulating circuit 17 is connected on the input side to the battery 13 for energy supply, and provides an output voltage whose amplitude can be quasi-infinitely varied between 560 V and 800 V. Following the charging phase, which is of a predetermined length, the selected buffer capacitor $C_1$, $C_2$ or $C_3$ is separated from the voltage-regulating circuit 17 by the switching means 16, and connected via the output resistor R to the stimulation electrode 18.1, so the buffer capacitor $C_1$, $C_2$ or $C_3$ is discharged via the heart 5 and the ground electrode 18.2, and emits a defibrillation pulse. Because of the relatively high pulse intensity, the stimulation electrode 18.1 is configured to have a large surface, like the mass electrode 18.2 and in contrast to the detection electrode 3, for preventing burning of or damage to tissue during the emission of the high-energy defibrillation pulses.

The temporal control of the switching means 16 for charging the buffer capacitors and emission of the defibrillation pulse is effected by the control unit 19. Furthermore, the control unit 19 permits an adaptation of the defibrillation energy to the individual defibrillation threshold of the patient in that either the charging voltage provided by the voltage-regulating circuit 17 or the capacity of the buffer capacitor is changed. The control unit 19 is therefore connected on the output side to the voltage-regulation circuit 17 for setting the charge voltage, and to the switching means 16 for selecting one of the buffer capacitors $C_1$, $C_2$, $C_3$.

The buffer capacitor is subsequently separated again from the stimulation electrode 18.1 by the switching means 16, ending the defibrillation pulse.

On the one hand, it is crucial for successful defibrillation that the buffer capacitor $C_1$, $C_2$ or $C_3$ be separated from the stimulation electrode 18.1 at the proper time, before the capacitor voltage drops below the rheobase value due to the discharge, because a further discharge does not have a defibrillating effect, but rather may initiate a refibrillation.

On the other hand, it is desirable to discharge the buffer capacitor $C_1$, $C_2$ or $C_3$ as completely as possible, because the residual charge remaining on the buffer capacitor $C_1$, $C_2$ or $C_3$ following a defibrillation pulse cannot be used at all, or cannot be used completely, and thus reduces the efficiency of the defibrillator 1, which is defined as the ratio of stored energy to released energy.

The defibrillator 1 therefore continuously measures the stimulation voltage during the emission of a defibrillation pulse, and ends the defibrillation pulse when the rheobase voltage is not met. To this end, the defibrillator 1 has a voltage-measuring device 20, which is connected on the input side to the connector for the stimulation electrode 18.1 and on the output side to the control unit 19 for measuring the defibrillation voltage, and being able to end the defibrillation pulse if necessary. When the rheobase voltage is attained, the control unit 19 generates a control signal for the switching means 16, which then separate the buffer capacitor $C_1$, $C_2$ or $C_3$ from the stimulation electrode 18.1 and thus end the defibrillation pulse. This advantageously prevents a defibrillation pulse from having a refibrillating effect when the defibrillation voltage drops below the rheobase voltage, on the one hand. On the other hand, with the continuous measurement of the defibrillation voltage during discharge of the buffer capacitor $C_1$, $C_2$ or $C_3$, a safety margin between the defibrillation voltage and the rheobase voltage can be omitted, so the buffer capacitor $C_1$, $C_2$ or $C_3$ can be discharged to the rheobase voltage, increasing the service life of the battery.

Figure 2:
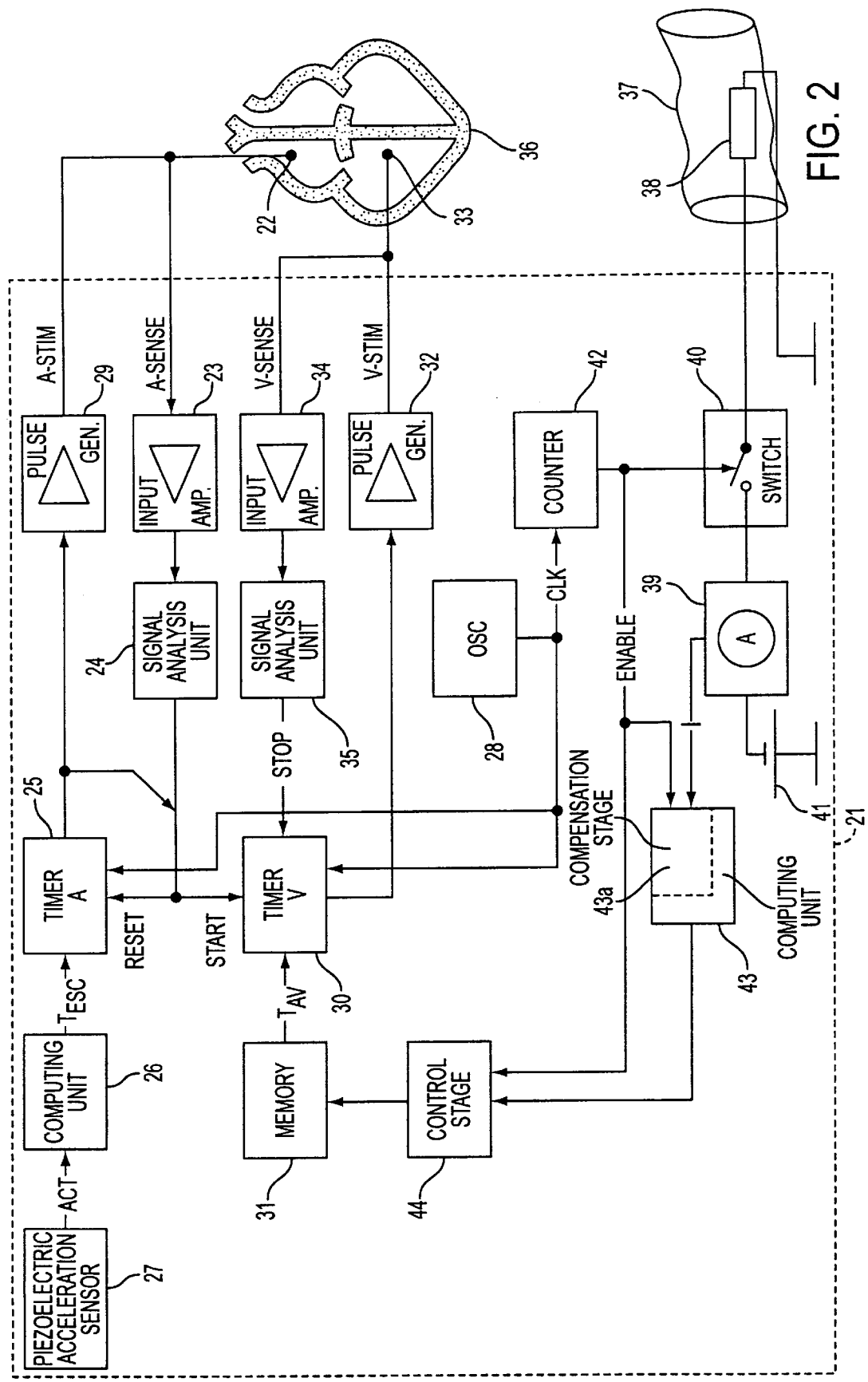
FIG. 2 is a further embodiment, a cardiac pacemaker in which the cardiac pumping performance is measured by a hemodynamic sensor for optimizing the AV transmission time.

FIG. 2 shows, as a second embodiment of the invention, a rate-adaptive, dual-chamber pacemaker 21, for treating a disturbed stimulation transmission from the atrium to the ventricle. For this purpose, the illustrated pacemaker 21 employs an endocardially-positioned (in the atrium) electrode 22 to detect spontaneous cardiac signals, which are first supplied to an input amplifier 23 and, afterward, to a signal-analysis unit 24 for detecting a spontaneous atrial action occurring as a P-wave in the detected cardiac signals. When this type of P-wave is detected, the signal-analysis unit 24 generates a control signal that initializes the counter 25, with the starting value of the counter 25 being calculated by the computing unit 26 from the activity signal ACT, which is generated by the piezoelectric acceleration sensor 27 and indicates the physical activity of the pacemaker patient. With each clock pulse of the oscillator 28, the counter 25 reduces its counting value to zero, whereupon the counter 25 transmits a control signal to the pulse generator 29, which then generates a stimulation pulse and supplies it to the atrium via the electrode 22.

Furthermore, the illustrated pacemaker 21 permits a stimulation of the ventricle, which is particularly important in a disturbed stimulation transmission from the atrium to the ventricle. The stimulation in the ventricle is effected with a delay by a predetermined AV transmission time following the preceding spontaneous or stimulated atrial action, so the ventricle can fill as completely as possible with blood prior to the contraction to attain the greatest possible heart minute volume with a predetermined heart rate.

The counter 30 for the time control of the ventricle is therefore connected on the input side to the signal-analysis unit 24, on the one hand, and to the counter 25 for the atrial time control, on the other, for starting an AV transmission time with a spontaneous as well as a stimulated atrial action, with the starting value for the counter 30 being stored in the memory element 31. With each clock pulse of the oscillator 28, the counter 30 decrements the counting value to zero, whereupon a control signal is transmitted to the pulse generator 32, which then generates a stimulation pulse and transmits it to the ventricle via the electrode 33. The stimulation of the ventricle is not necessarily effected following each atrial action, but can be inhibited by a spontaneous ventricle action during the AV transmission time. For this purpose, the electrode 33 disposed in the ventricle is connected to an input amplifier 34 and a downstream signal-analysis unit 35 for detecting a spontaneous ventricle action occurring as a QRS complex in the detected cardiac signals. In a detection of this type of QRS complex, the signal-analysis unit 35 generates an inhibition signal that is supplied to the counter 30, which then terminates its counting process and thus generates no stimulation pulse.

The pacemaker 21 permits an automatic setting of the AV transmission time.

Using a hemodynamic sensor, the pacemaker 21 measures the flow speed of the blood in the vena cava 37 to permit an assessment of the pumping performance of the heart 36. The hemodynamic sensor essentially comprises a resistor element 38 that is disposed in the vena cava and has a temperature-dependent electrical resistor that is connected by way of the current-measuring device 39 and the controllable switching element 40 to the battery 41 during a measuring process, causing the resistor element 38 to heat up due to the ohmic losses inside it.

Because the measurement of the flow speed through the resistor element 38 is associated with an additional current consumption, the measurement is not effected continuously, but at respective, programmed times, for example at intervals of a few hours. For this purpose, the illustrated pacemaker 21 includes a further counter 42, which is likewise actuated by the oscillator 28, and when a certain counter state is attained, the counter generates a control signal that is supplied to the controllable switching element 40, whereupon this element connects the resistor element 38 to the battery 41 by way of the current-measuring device 39.

The temperature of the resistor element 38 increases until an equilibrium is established between the supplied energy and the energy that is completely converted into heat in the resistor element 38, on the one hand, and the thermal energy that is carried off by the blood flowing past through heat conduction and convection, on the other hand. Because the energy carried off through convection increases with the blood flow speed, a dependency exists between the temperature of the resistor element 38 and the blood flow speed. Hence, at low flow speeds, only a small quantity of heat is dissipated through convection, so a relatively large temperature gradient at the resistor element 38, and thus a correspondingly high temperature, are necessary for dissipating the supplied electrical energy. At high flow speeds, in contrast, more heat is carried off through convection, so the proportion of heat energy is lower, and therefore a smaller temperature gradient at the resistor element 38 suffices to maintain the energy balance of the resistor element 38 at an equilibrium. The temperature of the resistor element 38 thus reflects the flow speed of the blood, and can be calculated simply from the current flux through the resistor element 38 based on the temperature-dependent electrical conductivity of the resistor element 38. The output signal of the current-measuring device 39 is therefore supplied to the computing unit 43 as a measure for the flow speed; from this signal, the unit calculates the heart time volume (HTV) that represents the pumping performance. The computing unit 43 encompasses a compensation stage 43a for compensating long-term measurement fluctuations due to fluctuations in the base temperature. This stage is activated by the controllable switching element 40 at the start of each measuring process, that is, prior to the connection of the resistor element and the battery 41, and internally provides a correction value that is incorporated into the calculation result of the unit 43.

The AV transmission time is optimized by a control stage 44, which is connected on the input side to the computing unit 43 and receives the heart minute volume as an optimization criterion. On the output side, the control stage 44 is connected to the memory element 31, which respectively receives the instantaneous value of the AV transmission time and holds it between individual measuring processes of the hemodynamic sensor.

Figure 3B:
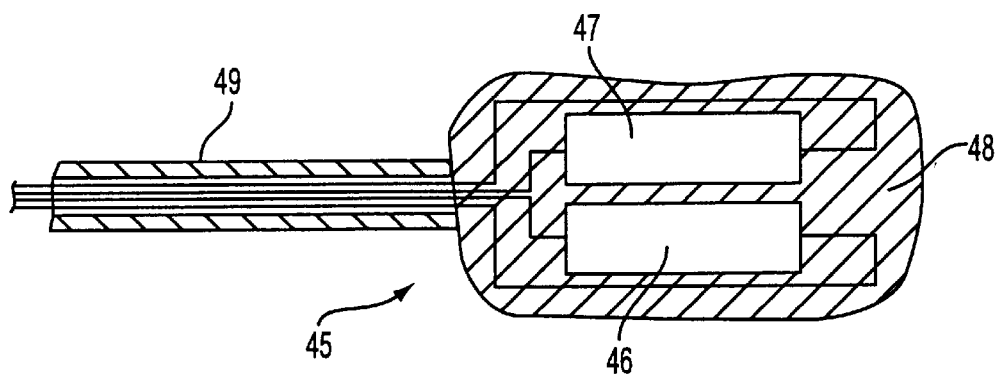
FIG. 3b is a alternative embodiment of a hemodynamic sensor.

FIG. 3b shows an alternative embodiment of a hemodynamic sensor 45, which essentially differs from the sensor 4 described above and shown in FIG. 3a in that the resistor element 46 is not heated due to the ohmic losses occurring inside it, but by a separate heating element. This heating element also comprises a resistor element 47, which is connected to a current or voltage source for heating, and is therefore heated by the ohmic losses occurring inside it. The resistor element 46 serving in measurement is heated through heat conduction between the two resistor elements 46, 44. To prevent an electrical contact with the blood flowing past, the two resistor elements 46, 47 are encapsulated by an electrically-insulating but thermally well-conducting mass 48.

FIG. 5 shows a further embodiment of a hemodynamic sensor. In this sensor, the impedance of the blood in a blood vessel 50 is measured, which, in a range below about 10 kHz (in which the erythrocytes can actually be observed as insulators, according to the inventor), is dependent on the flow speed as a result of the more or less uniform orientation of the erythrocytes, which is dependent on the flow speed.

The impedance measurement is effected by two measuring electrodes 51.1, 51.2 that are disposed in the wall of a catheter 52 whose distal end is fixed in the ventricle and supports the stimulation electrode. The integration of the hemodynamic sensor into the catheter 52, which is necessary anyway, advantageously permits the implantation of the stimulation arrangement without additional surgical efforts. This also counteracts a dislocation of the measuring electrodes 51.1, 51.2 and assures a spatial fixing of the two measuring electrodes 51.1, 51.2 relative to one another. The two measuring electrodes 51.1, 51.2 are disposed in a region of the catheter 52 which, in the implanted state, lies outside the heart inside a segment of a blood vessel in which an essentially laminar flow occurs, so the determination of the flow speed is not impeded by flow turbulence.

To measure impedance, a signal generator 53 that is integrated into the stimulator, operates in a range between 0.1 Hz and 10 kHz and supplies a sinusoidal measuring or sampling voltage of ±1 V, generates an electric test signal that is supplied to the two measuring electrodes 51.1, 51.2 by way of two electrical lines 54.1, 54.2 extending inside the catheter 52 and a series resistor 53a of 10 kΩ for reducing the measured current. An effective-voltage measuring device 55 switched between the two measuring lines 54.1, 54.2 measures the effective value of the voltage drop between the measuring electrodes 51.1, 51.2. The signal obtained in this manner is then supplied to an evaluation unit 56 that uses the signal to calculate the impedance of the blood and, depending on the result, determines the blood flow in the blood vessel 50—based on a previously-stored characteristic—that reflects the heart time volume (HTV) and permits an optimization of the stimulation behavior.

The invention is not limited in its embodiment to the above-disclosed, preferred embodiments. Rather, numerous variations are conceivable that use the illustrated solution, even in fundamentally-different embodiments.

What is claimed is:

1. An implantable stimulator for treating arrhythmic function disturbances of a heart, comprising:
   a stimulation electrode for transmitting stimulation pulses to the heart, the electrode being adapted to be disposed in one of the heart and the vicinity thereof;
   pulse generator that is connected on an output side to the stimulation electrode for generating the stimulation pulses;
   a control unit that is connected on an output side to the pulse generator for controlling the pulse emission by the pulse generator;
   a hemodynamic sensor for controlling the pulse emission as a function of the cardiac pumping performnance, the hemodynamic sensor including;
   two measuring electrodes spaced apart and adapted to be located outside of the heart and one of in a blood vessel and in electrical contact with a blood vessel, for measuring the blood impedance dependent on the blood vessel throughput;
   a signal generator that generates an AC voltage in a range below 10 kHz for generating a test signal for impedance measurement, the generator being coupled to the two measuring electrodes for generating an electrical field between the two measuring electrodes;
   an electrical measuring device having an input side connected to the two measuring electrodes for determining the blood vessel throughput as a function of a measured electrical signal from the two measuring electrodes; and
   a blood vessel throughput signal-analysis unit having an input side connected to the electrical measuring device and having an output side connected to the control unit for recognizing an arrhythmic cardiac function disturbance using the measured throughput quantity.

2. The stimulator according to claim 1, wherein the control unit is connected on an input side to the stimulation electrode for detecting spontaneous cardiac signals and for controlling the pulse emission as a function of both the measured blood throughput and the spontaneous cardiac signals, and includes a first cardiac signal analysis unit having an input side connected to the output of the electrode for recognizing a cardiac function disturbance using the measured spontaneous cardiac signals.

3. The stimulator according to claim 2, wherein the control unit includes a logic unit for evaluating both the measured blood throughput and the cardiac signals, the logic unit being connected on an input side to the cardiac signal analysis unit for assessing the cardiac signals, and to the blood throughput signal-analysis unit for assessing the cardiac pumping performance.

4. The stimulator according to claim 1, further comprising a controllable switching element for switching the hemodynamic sensor on and off.

5. The stimulator according to claim 4, wherein a control input of the controllable switching element is connected to an output of the cardiac signal analysis unit for switching on the sensor when a disturbance in the cardiac function is detected by the cardiac signal analysis unit and for switching off the sensor when a cardiac function that has been corrected is detected by the cardiac signal analysis unit.

6. The stimulator according to claim 4, wherein the control input of the controllable switching element is connected to one of a timer for switching the hemodynamic sensor on and off with time control, and a telemetry receiver for remote-controlled switching on and off by an extracorporeal control device.

7. The stimulator according to claim 1, wherein the two measuring electrodes are adapted to be disposed in one of (1) one behind the other in the flow direction for longitudinal impedance measurement and (2) adjacently to one another transversely to the flow direction, for transversal impedance measurement.

8. The stimulator according to claim 1, wherein the hemodynamic sensor is adapted to be disposed in one of the vena cava and the pulmonary artery.

9. The stimulator according to claim 1, wherein a measuring voltage in a range of 0.3 V to 3 V, and a measuring current in a range of 10 $\mu$A to 100 $\mu$A are set by the signal generator and the series resistor.

10. The stimulator according to claim 1, further including means are connected to an input of the blood throughput signal analysis unit, for compensating for at least one of the influence of temperature- and medication-stipulated changes in the blood throughput.

11. The stimulator according to claim 1, wherein the control unit has an input side connected to a further electrode for detecting spontaneous cardiac signals and the control unit further includes a cardiac signal analysis unit having an input side connected to the output of the electrode for recognizing a cardiac function disturbance using the measured spontaneous cardiac signals and for controlling the pulse emission as a function of both the measured blood throughput and the spontaneous cardiac signals.

* * * * *